United States Patent [19]

Elliott et al.

[11] Patent Number: 4,874,781
[45] Date of Patent: Oct. 17, 1989

[54] PESTICIDES

[75] Inventors: Michael Elliott, Stevenage; Norman F. Janes, Luton; Bhupinder P. S. Khambay, Harrow Weald, all of England

[73] Assignee: National Research Development Corporation, London, United Kingdom

[21] Appl. No.: 143,319

[22] Filed: Jan. 11, 1988

Related U.S. Application Data

[63] Continuation of Ser. No. 903,452, Sep. 4, 1986, abandoned.

[30] Foreign Application Priority Data

Sep. 4, 1985 [GB] United Kingdom ................. 8521943

[51] Int. Cl.$^4$ .................... A01N 37/10; A01N 37/34; C07D 317/52; C07C 69/612
[52] U.S. Cl. .................... 514/463; 514/464; 514/521; 514/532; 549/447; 549/442; 549/433; 558/398; 560/105
[58] Field of Search ............... 560/105, 100, 56, 55; 558/398; 549/447, 442, 433; 514/532, 521, 464, 463

[56] References Cited

U.S. PATENT DOCUMENTS

| | | | |
|---|---|---|---|
| 4,238,406 | 12/1980 | Suzuki et al. | 558/398 |
| 4,239,777 | 12/1980 | Berkelhammer et al. | 558/398 |
| 4,260,633 | 4/1981 | Anderson et al. | 558/398 |
| 4,422,978 | 12/1983 | Suzuki et al. | 558/398 |

FOREIGN PATENT DOCUMENTS 8240440 3/1982 Japan.

*Primary Examiner*—Nicky Chan
*Attorney, Agent, or Firm*—Nixon & Vanderhye

[57] ABSTRACT

A compound of formula I

I: $ArCHR_1CO_2CHDR_2$ in which formula:

Ar represents a phenyl or naphthyl group optionally substituted by one or more halogen, alkoxy, haloalkoxy, methylenedioxy, $C_1$-$C_6$ alkyl or haloalkyl groups;

$R_1$ represents the group $-CH(CF_3)CH_3$ or $-C(CF_3)=CH_2$ $R_2$ represents the residue of an alcohol $R_2CHDOH$ in which D is hydrogen or cyano and of which the [1R, cis]2,2-dimethyl-3-(2,2-dibromovinyl)cyclopropane carboxylic ester is significantly insecticidal.

6 Claims, No Drawings

PESTICIDES

This application is a continuation of Ser. No. 903,452, filed Sept. 4, 1986, now abandoned.

This invention relates to pesticides and in particular to pesticidal compounds, the production of such compounds, intermediates for use in their production, compositions containing such compounds and the use of such compounds and compositions for pest control.

Compounds have now been discovered formulations of which, are effective against a range of insect and other pests.

Accordingly the present invention comprises a compound of formula I

I: $ArCHR_1CO_2CHDR_2$ in which formula:

Ar represents a phenyl or naphthyl group optionally substituted by one or more halogen, alkoxy, haloalkoxy, methylenedioxy, $C_1$-$C_6$ alkyl or haloalkyl groups;

$R_1$ represents the group $-CH(CF_3)CH_3$ or $-C(CF_3)=CH_2$ $R_2$ represents the residue of an alcohol $R_2CHDOH$ in which D is hydrogen or cyano and of which the [1R, cis]2,2-dimethyl-3-(2,2-dibromovinyl) cyclopropane carboxylic ester is significantly insecticidal.

Ar is typically substituted phenyl and substitution is usually at the 3-(meta) and/or 4-(para)-position by fluorine, bromine, chlorine, a $C_1$-$C_6$ alkyl group e.g. methyl or tertbutyl, a $C_1$-$C_6$ alkoxy group e.g. methoxy, ethoxy, a halomethoxy or haloethoxy group, which may comprise one or more halogens, e.g. $OCF_3$, $OCF_2H$ or a halomethyl or haloethyl group e.g. $CF_3$. Ar generally carries no more than two substituents, and typically only one, preferably chlorine.

When the compound of formula I is chiral it can of course exist in different stereoisomeric forms. Both mixtures of stereoisomers and single stereoisomers are included within the scope of the present invention.

$R_2CHD$ may represent the residue of an alochol of formula $R_2CHDOH$ claimed or described in the specification for UK Patent No. 1413491 which gives rise to significant insecticidal activity when esterified with [1R, cis]-2,2-dimethyl-3-(2,2-dibromovinyl) cyclopropane carboxylic acid. Such activity is usually at least 5 towards houseflies relative to bioresmethrin=100 and may be 10 or more.

Typically $R_2CHD$ represents the residue of an alcohol $R_2CHDOH$ which is a phenoxy, benzyl or benzoyl substituted benzyl or α-cyano benzyl alcohol. 3-Phenoxybenzyl, 4-fluoro-3-phenoxybenzyl, α-cyano-3-phenoxybenzyl and α-cyano-4-fluoro-3-phenoxybenzyl residues are of particular interest.

The present invention also includes within its scope a process for the production of a pesticidal compound of formula I in which an acid of formula II $ArCHR_1CO_2H$ or an esterifiable derivative thereof e.g. an ester, acyl halide, alkali metal or ammonium salt is reacted with an alcohol of formula $R_2CHDOH$ or an esterifiable derivative thereof e.g. an alkli metal salt thereof.

The present invention further includes within its scope such intermediate acids and esterifiable derivatives thereof.

Saturated and unsaturated acids and derivatives ($R_1$=$CH(CF_3)$ $CH_3$ or $C(CF_3)$=$CH_2$) may be produced from the mixture of isomers of formula III: $ArCH(CH(CF_3)=CH_2)CO_2R$ and IV: $ArC(CO_2R)=C(CF_3)CH_3$ (wherein R represents $C_1$-$C_6$ alkyl or benzyl) obtainable by dehydration of the compound $ArCH(CO_2R)C(OH)(CF_3)CH_3$ (V) using for example phosphorous trichloride in a solvent such as pyridine. Compounds V may be produced by reaction of the ketone $CF_3COCH_3$ with compounds (VI): $ArCHBrCO_2R$ in the presence of a metal such as zinc or a complex thereof such as $Et_2Al$ $Cl/Zn/CuBr$ or by reaction with compounds VII: $ArCH_2CO_2R$ in the presence of a base such as lithium diisopropylamine (LDA).

Compound IV may be isomerised to isomer III using a basic reagent such as LDA, III being hydrolysed to the corresponding acid convertible to final compounds I by esterification or to a diastereoisomeric mixture of saturated acids of formula II by hydrogenation, suitably using a catalyst at high pressures. Such a mixture may be esterified to give a diastereoisomeric mixture of compounds I followed by isomer separation or separated into diastereoisomers prior to final esterification.

In a variation of the immediately foregoing procedure, the mixture of esters III and IV is hydrolysed to give an isomeric mixture of acids followed by isomerisation of the acid corresponding to IV to the acid corresponding to III by means of a base.

Compounds of formula I can be used to combat pest infestation in the domestic, horticultural or agricultural or medical, including veterinary, areas.

The present invention also includes within its scope a process for the production of a pesticidal composition which comprises formulating a compound of formula I with an inert carrier or diluent and compositions thereby produced.

Compositions may be in the form of dusts, granular solids, wettable powders, mosquito coils and other solid preparations or as emulsions, emulsifiable concentrates, sprays and aerosols and other liquid preparations after the addition of appropriate solvents, diluents and surface-active agents.

Agriculturally and horiticulturally applicable compositions, which require the active ingredient to possess significant photostability are of particular interest.

The pesticidal compositions of the invention normally contain from 0.001 to 25% by weight of the compound of formula I but the compositions can contain higher concentrations of active ingredient of formula I e.g. up to 95% in compositions to be sold as concentrates for dilution before use by the ultimate user.

The compositions of the invention can, depending on the intended application, include diluents such as hydrocarbon oils, e.g. xylene or other petroleum fractions, water, anionic, cationic or non-ionic surface-active agents, anti-oxidants and other stabilisers as well as perfumes and colouring matters. These inert ingredients may be of the type and in proportions such as are conventionally used in pesticidal compositions containing pyrethroid-like compounds.

In addition to these inactive ingredients, the compositions of the present invention may contain one or more further active ingredients which may be other pesticidal compounds of the pyrethroid type or of other types and the composition may also include synergists particularly those of a type known to be capable of synergising the activity of natural pyrethrin and pyrethroid-like insecticides. Sinergists of this type include piperonyl butoxide, tropital and sesamex.

Compounds of formula I may be applied in such a manner that pest infestation is diminished or prevented or both.

In accordance with a further aspect of the present invention, a method of pest control comprises treating a pest or a surface or environment susceptible to pest infestation with an effective amount of a compound of formula I.

The compounds or compositions of the invention can be used as insecticides or acaricides for example in a domestic environment in spraying rooms to combat infestation with houseflies or other insects, they can be used for treatment of stored crops or cereals to combat infestation by insects or other pests, they can be used to spray growing crops, e.g. cotton to combat infestation by common pests and they can be used in the medical or veterinary field, e.g. as a cattle spray to prevent or treat infestation by insects or other pests.

The compounds are of particular interest for the control of pests such as the following:

from the class of the Isopoda, for examle Oniscus asellus, Armadillidium vulgare and Porcellio scaber;

from the class of the Diplopoda, for example Blaniulus guttulatus;

from the class of the Chilopoda, for example Geophilus carpophagus and Scutigera spec;

from the class of the Symphyla, for example Scutigerella immaculata;

from the order of the Thysanura, for example lepisma saccharine;

from the order of the Collembola, for example Onychiurus armatus;

from the order of the Orthoptera, for example Blatta orientalis, Periplaneta americana, Leucophaea madarae, Acheta domesticus, Cryllotalpa spp., Locusta migratoria migratorioides, Melanoplus differentialis and Schistocerca gregaria;

from the order of the Dermaptera, for example Forficula auricularia;

from the order of the Isoptera, for example Reticulitermes spp;

from the order of the Anoplura, for example Phylloxera vastatrix, Pemphigus spp., Pediculus humanus corporis, Haematopinus spp. and Linognathus spp;

from the order of the Mallophaga, for example Trichodectes spp. and Demalinea spp;

from the order of the Thysanoptera, for example Hercinothrips fermoralis and Thrips tabaci;

from the order of the Heteroptera, for example Eurygaster spp., Dysdercus intermedius, Piesma quadrata, Cimex lectularius, Rhodnius prolius and Triatoma spp;

From the order of the Homoptera, for example Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae, Myzus spp., Phorodon humuli, Rhopalosiphum padi, Empoasca spp., Euscelis bilobatus, Lecanium corni, Saissetia oleae, Laodelphax striatellus, Aondiiella aurantii, Aspidiotus hederae, Pseudococcus spp. and Psylla spp;

from the order of the Lepidoptera, for example Pectinophora gossypiella, Bupalus piniarius, Cheimatobia brumata, Lithocolletis blancardella, Hyponomeuta padella, Plutella maculipennis, Malacosoma neustria, Euproctis Chrysorrhoea, Lymantria spp., Bucculatrix thurberiella, Phyllocnistis citrella, Agrotis spp., Euxoa spp., Feltia spp., Earias insulana, Laphygma exigua, Mamestra braxsicae, Panolis flammea, Prodenia litura, Trichoplusia ni, Carpocapsa pomonella, Fieris spp., Pyrausta nubilalis, Ephestia kuehniella, Galleria mellonella, Cacoecia podana, Capua reticulana, Choristoneura fumiferana, Clysia ambiguella, Homona magnanima and Tortrix viridana;

from the order of the Coleoptera, for example Anobium punctatum, Thizopertha dominica, Bruchidius obtectus, Acanthoscelides obtectus, Hylotrupes bajulus, Agelastica alni, Leptinotarsa decemlineata, Phaedon cochleariae, Diabrotica spp., Psylliodes chrysocephala, Epilachna varivestis, Atomaria spp., Oryzaephilus surinamensis, Sitophilus spp., Otiorrhynchus sulcatus, Cosmoplites sordidus, Geuthorrhynchus assimilis, Hyperapostica, Dermestes spp., Trogoderma spp., Anthrenus spp., Attagenus spp., Lyctus spp., Meligethes aeneus, Ptinus spp., Niptus hololeucus, Gibbium psylloides, Tribolium spp., Tenebrio molitor, Agriotes spp., Conoderus spp., Melolontha melolontha, Amphimallon solstitialis and Costelytra zealandica;

from the order of the Hymenoptera, for example Diprion spp., Hoplacampa spp., Lasius spp., Monomorium pharaonis and Vespa spp., from the order of the Diptera, for example Aedes spp., Anopheles spp., Culex spp., Drosophila melanogaster, Musca spp., Fannia spp., Calliphora erythrocephala, Lucilia spp., Chrysomyia spp., Cuterebra spp., Gastrophilus spp., Hyppobosca spp., Stomoxys spp., Oestrus spp., Hypoderma spp., Tabanus spp., Tannia spp., Bibio hortulanus, Oscinella frit, Phorbia spp., Pegomyia hyoscyami, Ceratitis capitata, Dacus oleae and Tipula paludosa;

from the order of the Siphonaptera, for example Xenopsylla cheopis and Ceratophyllus spp.;

from the class of the Arachnida, for example Scorpio maurus and Latrodectus mactans;

from the order of the Acarina, for example Acarus siro, Argas spp., Ornithodoros spp., Dermanyssus gallinae, Eriophyes ribis, Phyllocoptruta oleivora, Boophilus spp., Rhipicephalus spp., Amblyomma spp., Hyalomma spp., Ixodes spp., Psoroptes spp., Chorioptes spp., Sarcoptes spp., Tarsonemus spp., Bryobia praetiosa, Panonychus spp. and Tetranychus spp.

The invention is illustrated by the following Examples:

Temperatures are in °C.

EXAMPLE 1

A. Ethyl-2-(4-chlorophenyl)-2-bromoethanoate

Benzoyl peroxide (0.1 g) is added to a stirred mixture of ethyl-2-(4-chlorophenyl)ethanoate (14 g) and N-bromosuccinimide (16 g) in carbon tetrachloride (200 ml), and the mixture refluxed for 2 hours, filtered, solvent evaporated under reduced pressure and the residue distilled. B.p. 114°–116° C. at 0.4 mmHg. Yield 15 g. $n_D1.5510$.

B. Ethyl-2-(4-chlorophenyl)-3-hydroxy-3-methyl-4.4.4-trifluorobutanoate

1M Diethylaluminium chloride (24 ml) is added to a stirred suspension of cuprous bromide (0.16 g) and zinc dust (2.1 g) in dry tetrahydrofuran (THF) (80 ml) under an atmosphere of nitrogen at $-20°$ C. and then stirred at 20° C. for 1 hour and finally cooled to $-30°$ C. A solution of ethyl-2-(4-chlorophenyl)-2-bromoethanoate (5.5g) and 1,1,1-trifluoroacetone (4 g) in dry THF (20 ml) is added over 30 minutes and allowed to warm up to room temperature over 1 hour. Saturated ammonium chloride solution is added and after concentrating under reduced pressure, extracted with ether (×3), washed with water, dried and the solvent evaporated. The residue is purified by flash chromatography on silica eluted with 8% ether in petroleum ether b.p. 60°–80° C. Yield 5 g $n_D$ 1.4832 b.p. 106°–110° at 0.2 mmHg.

C. Mixture of ethyl-2-(4-chlorophenyl)-3-(trifluoromethyl)-but-3-enoate and ethyl-2-(4-chlorophenyl)-3-(trifluoromethyl)-but-(E/Z)-enoate To a stirred solution of ethyl-2-(4-chlorophenyl)-3-hydroxy-3-methyl-4,4,4-trifluorobutanoate (2.7 g) in pyridine (5 ml) is added phosphoryl chloride (5 ml) whilst maintaining the temperature below 30° C. After the addition, the mixture is heated at reflux for 2 hours, poured into water, extracted with ether (×3), washed successively with 2N aqueous hydrochloric acid, water, dried and the solvent evaporated under reduced pressure. Yield 2.5 g $n_D$ 1.4822.

D. Ethyl-2-(4-chlorophenyl)-3-(trifluoromethyl)-but-3-enoate 1.6M Butyllithium (6.2 ml) is added to a stirred solution of diisopropylamine (1.1 g) in dry THF (15 ml) under an atmosphere of nitrogen at −78° C. After 15 minutes a solution of olefinic ethyl esters 1.3 g) from Procedure C in THF (5 ml) is added over 1 minute and the mixture stirred at −78° C. for 1 hour and then warmed to −10° C., saturated aqueous ammonium chloride solution is added, the mixture concentrated under reduced pressure, extracted with ether (×3), washed with 2N aqueous hydrochloric acid, dried, and the solvent evaporated off under reduced pressure. The residue is purified by flash chromatography on silica gel eluted with 3% ether in petroleum ether b.p.60°–80° C. Yield 1.08 g $n_D$1.4730.

E. 2-(4-chlorophenyl)-3-(trifluoromethyl)-but-3-enoic acid

15% Aqueous sodium hydroxide (3 ml) is added to a stirred solution of ethyl-2-(4-chlorophenyl)-3(trifluoromethyl)-but-3-enoate (0.3 g) and the mixture refluxed for 3 hours, cooled to room temperature, diluted with water (10 ml) and extracted with ether. The aqueous phase is acidified with 2N aqueous hydrochloric acid extracted with ether (×3), dried and the solvent evaporated under reduced pressure. Yield 0.25 g $n_D$1.4898.

F. 2-(4-chlorophenyl)-3-(trifluoromethyl)-butanoic acid

5% Pd/C (0.1 g) is added to a stirred solution of 2-(4-chlorophenyl)-3-(trifluoromethyl)-but-3-enoic acid (0.5 g) in absolute methanol (10 ml) and the mixture stirred under an atmosphere of hydrogen (20 bars) for 20 hours at 20° C. The mixture is filtered and the solvent evaporated under reduced pressure to give the product. Yield 0.5 g semi solid.

Similarly, Ethyl-2-(4-chlorophenyl)-3-(trifluoromethyl)-but-3-enoate is hydrogenated to ethyl-2-(4-chlorophenyl)-3-(trifluoromethyl)-butanoate $n_D$1.4709.

G. (3-Phenoxybenzyl)-2-(4-chlorophenyl)-3-trifluromethyl)butanoate

Oxalylchloride (1 ml) is added to a stirred solution of 2-(4-chlorophenyl)-3-(trifluoromethyl)-butanoic acid (0.25 g) in dry benzene (10 ml). After 24 hours, the solvents are removed under reduced pressure and the residual acid chloride, dissolved in dry benzene is added to a stirred solution of 3-phenoxybenzyl alcohol (0.25 g) and pyridine (0.2 ml) in dry benzene (3 ml). After 2 hours, the mixture is concentrated under reduced pressure and purified by thin layer chromatography eluted with 8% ether in petroleum ether b.p. 60°–80° C. Yield 0.3 g $n_D$1.5372 (Reference 7058). This product is separated by HPLC using Lichroprep Si 60 eluting with 2.5% ether in petroleum ether b.p.60°–80° C. into two components: LP (Less Polar) Yield 0.03 g, $n_D$1.5368 (Reference 7082) and MP (More Polar) Yield 0.1 g, $n_D$1.5302 (Reference 7083).

EXAMPLE 2

In an alternative procedure the mixture of olefinic esters from Example 1, Procedure C is hydrolysed by the method of Example 1, Procedure E to give a mixture of olefinic acids (75% exo and 25% conjugated) $n_D$1.4958, which is then isomerised by the method of Example 1, Procedure D to give 2-(4-chlorophenyl)-3-(trifluoromethyl)-but-3-enoic acid.

EXAMPLE 3–11

The following compounds (I) are prepared from the respective acids and alcohols by following the Procedures of Examples 1 or 2:

| Example No. | Compound | Reference |
|---|---|---|
| 3 | 5-Benzyl-3-furyl-2-(4-chlorophenyl)-3-trifluoromethyl-but-3-enoate $n_D$1.5312 | 7055 |
| 4 | 3-Phenoxybenzyl-2-(4-chlorophenyl)-3-trifluoromethyl-but-3-enoate $n_D$1.5504 | 7014 |
| 5 | (4-Fluoro-3-phenoxybenzyl)-2-(4-chlorphenyl)-3-trifluoromethyl-but-3-enoate $n_D$1.5322 | 7125 |
| 6 | (α-Cyano-3-phenoxybenzyl)-2-(4-chlorophenyl)-3-trifluoromethyl-but-3-enoate $n_D$1.5428 | 7054 |
| 7 | (α-Cyano-4-fluoro-3-phenoxybenzyl)-2-(4-chlorophenyl)-3-trifluoromethyl-3-but-3-enoate. $n_D$1.5292 | 7123 |
| 8 | (5-Benzyl-3-furylmethyl)-2-(4-chlorophenyl)-3-butanoate. $n_D$1.5190 | 7121 |
| 9 | (4-fluoro-3-phenoxybenzyl)-2-(4-chlorophenyl)-3-trifluoromethyl-3-butanoate. $n_D$1.5232 | 7122 |
| 10 | (α-Cyano-3-phenoxybenzyl)-2-(4-chlorophenyl)-3-trifluoromethyl-3-butanoate $n_D$1.5278 | 7059 |
| 11 | (α-Cyano-4-fluoro-3-phenoxybenzyl)-2-(4-chlorophenyl)-3-butanoate. $n_D$1.5048 | 7126 |

Pesticidal activity is assessed against houseflies and mustard beetles by using the following techniques:

Houseflies (Musca domestica)

Female flies are treated on the thorax with a one microliter drop of insecticide dissolved in acetone. Two replicates of 15 flies are used at each dose rate and 6 dose rates are used per compound under test. After treatment, the flies are maintained at a temperature of 20° C.±1° and kill is assessed 24 and 48 hours after treatment $LD_{50}$ values are calculated in mocrograms of insecticide per fly and relative toxicities are calculated from the inverse ratios of the $LD_{50}$ values (see Sawicki et al, Bulletin of the World Health Organisatiion, 35, 893, (1966) and Sawicki et al, Entomologia and Exp. Appli 10 253, (1967)).

Mustard Beetles (Phaedon cochlaeriae Fab)

Acetone solutions of the test compound are applied ventrally to adult mustard beetles using a micro drop applicator. The treated insects are maintained for 48 hours afer which time kill is assessesd. Two replicates of 40 to 50 mustard beetles are used at each dose level and 5 dose levels are used for each compound.

$LD_{50}$ values and thence relative potencies are calculated as for houseflies.

For both insect species relative potencies are calculated by comparison with 5-benzyl-3-furylmethyl (1R)-trans-chrysanthemate (Bioresmethrin) which is one of the more toxic chrysanthemate esters known to houseflies and mustard beetle, its toxicity being about 24 times that of allethrin to houseflies and 65 times that of allethrin to mustard beetles.

Results

Relative potencies to Houseflies and Mustard Beetles (Bioresmethrin=100) are given under HF and MB respectively in the Table.

TABLE

Compounds of formula (1): $ArCHR_1CO_2CHDR_2$
(3POB = 3-phenoxybenzyl, 4F3POP = 4-fluoro-3-phenoxybenzyl, 5B3F = 5-Benzyl-3-furylmethyl, αCN3 POB = α-cyano-3-phenoxybenzyl, αCN4F3POB = α-cyano-4-fluoro-3-phenoxybenzyl, Ar = 4-chlorophenyl)

| Example | Reference | $R_1$ | —CHDR$_2$ | HF | MB |
|---|---|---|---|---|---|
| 1 | 7058 | CH$_3$CH(CF$_3$)— | 3POB | 3.6 | 1.5 |
| 1 | 7082 | " | 3POB(LP) | 2.5 | 2.2 |
| 1 | 7083 | " | 3POB(MP) | 2.3 | 1.5 |
| 3 | 7055 | CH$_2$=C(CF$_3$)— | 5B3F | 11 | 7.8 |
| 4 | 7014 | " | 3POB | 13 | 10 |
| 5 | 7125 | " | 4F3POB | 14 | 32 |
| 6 | 7054 | " | αCN3POB | 5.9 | 13 |
| 7 | 7123 | " | αCN4F3POB | 20 | 54 |
| 8 | 7121 | CH$_3$CH(CF$_3$)— | 5B3F | 7 | 2.3 |
| 9 | 7122 | " | 4F3POB | 4.7 | 6.3 |
| 10 | 7059 | " | αCN3POB | 3.9 | 4.4 |
| 11 | 7126 | " | αCN4F3POB | 14 | 26 |

We claim:
1. A compound of formula I

$$ArCHR_1C_2CHDR_2 \qquad I$$

in which formula:
Ar represents a phenyl or naphthyl group unsubstituted or substituted by one or more halogen, alkoxy, haloalkoxy, methylenedioxy, $C_1$-$C_6$ alkyl or haloalkyl groups;
$R_1$ represents the group —C(CF$_3$)=CH$_2$; and
$R_2$ CHD represents the residue of a benzyl, fluorobenzyl or α-cyanobenzyl alcohol substituted by a phenoxy, benzyl or benzoyl group.

2. A compound according to claim 1, in which Ar represents 4-chlorophenyl.

3. A compound according to claim 1 or 2, in which $R_2$CHD represents the residue of a phenoxy, benzyl or benzoyl substituted benzyl or α-cyanobenzyl alcohol.

4. A compound according to claim 1, in which $R_2$CHD represents 3-phenoxybenzyl, 4-fluoro-3-phenoxybenzyl, α-cyano-3-phenoxybenzyl or α-cyano-4-fluoro-3-phenoxybenzyl.

5. A compound according to claim 1, in which Ar represents substituted phenyl and —CHDR$_2$ represents 4-fluoro-3-phenoxybenzyl or α-cyano-4-fluoro-3-phenoxybenzyl.

6. A method of pest control, which method comprises treating a pest or a surface or environment susceptible to pest infestation with an effective amount of a compound of Formula I as defined in claim 1.

* * * * *